(12) United States Patent
Clarke

(10) Patent No.: US 7,208,008 B2
(45) Date of Patent: Apr. 24, 2007

(54) BALLOONLESS DIRECT STENTING DEVICE

(75) Inventor: Gerry Clarke, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 501 days.

(21) Appl. No.: 10/677,423

(22) Filed: Oct. 2, 2003

(65) Prior Publication Data

US 2005/0075710 A1    Apr. 7, 2005

(51) Int. Cl.
*A61F 2/06* (2006.01)
*A61M 29/02* (2006.01)
*A61M 25/00* (2006.01)

(52) U.S. Cl. ............... 623/1.11; 606/191; 606/198; 604/508; 604/509

(58) Field of Classification Search .......... 623/1, 623/1.11–1.13, 1.2, 1.23; 606/191–200, 606/108, 157, 110, 127; 604/104–109, 533, 604/96.01, 508–509

See application file for complete search history.

(56) References Cited

U.S. PATENT DOCUMENTS

| | | | |
|---|---|---|---|
| 4,921,478 A * | 5/1990 | Solano et al. ........... 604/509 |
| 5,108,416 A * | 4/1992 | Ryan et al. ............. 606/194 |
| 5,571,086 A * | 11/1996 | Kaplan et al. ......... 604/96.01 |
| 5,779,671 A | 7/1998 | Ressemann et al. | |
| 5,855,565 A | 1/1999 | Bar-Cohen et al. | |
| 5,902,333 A | 5/1999 | Roberts et al. | |
| 6,039,721 A * | 3/2000 | Johnson et al. ......... 604/508 |
| 6,217,585 B1 | 4/2001 | Houser et al. | |
| 6,238,410 B1 | 5/2001 | Vrba et al. | |
| 6,364,887 B1 | 4/2002 | Dworschak et al. | |
| 6,500,182 B2 * | 12/2002 | Foster ................... 606/127 |
| 6,544,278 B1 * | 4/2003 | Vrba et al. ............. 606/198 |
| 6,623,504 B2 * | 9/2003 | Vrba et al. ............. 606/192 |
| 6,733,521 B2 * | 5/2004 | Chobotov et al. ....... 623/1.12 |
| 2002/0161392 A1 * | 10/2002 | Dubrul ................. 606/200 |
| 2003/0032941 A1 | 2/2003 | Boyle et al. | |

* cited by examiner

*Primary Examiner*—Glenn K. Dawson
*Assistant Examiner*—Kathleen Sonnett

(57) ABSTRACT

A delivery system for a stent includes a catheter having an elongated inner member and at least one flexible, longitudinally oriented outer member that is operably attached to the distal portion of the inner member. A stent is placed concentrically around the flexible outer member, near the distal end of the catheter. When the elongated inner member is retracted, the flexible outer member folds longitudinally adjacent to the lumen of the stent causing the stent to be deployed. Another aspect according to the invention provides a method for delivering a stent to a treatment site within the vascular system.

20 Claims, 3 Drawing Sheets

BALLOONLESS DIRECT STENTING DEVICE

FIELD OF THE INVENTION

This invention relates generally to catheter deployment of stents. More specifically, the invention relates to a stent deployment system and method that uses a catheter but does not require a balloon to expand or place the stent at the target site.

BACKGROUND OF THE INVENTION

Balloon catheters are used in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel and improving blood flow. Soon after the procedure, however, a significant proportion of treated vessels re-narrow.

To prevent restenosis, short flexible mesh cylinders known as stents, constructed of metal or various polymers, are implanted within the vessel to maintain lumen size. Balloon-expandable stents are mounted on the periphery of the collapsed balloon portion of a balloon catheter at a diameter smaller than when deployed. During angioplasty, the balloon catheter carrying the stent is advanced through a network of tortuous blood vessels to the desired site. The balloon is inflated and expands the stent to a final diameter. After deployment, the stent remains in the vessel and the balloon is deflated, and the catheter is removed.

Although widely used, balloon catheters have significant limitations as stent delivery devices. The stent must be firmly attached to the exterior of the balloon, so that it does not become dislodged as the catheter passes through the vascular system to the target site. For this purpose, the stent is crimped to a sufficiently small diameter so that it grips the balloon. The shape of the balloon may be used to help secure the stent. Some catheter designs include sleeves that cover the ends of the stent, and stabilize it during passage through the vascular system.

The characteristics of the balloon including strength, flexibility and compliance are optimized to provide the desired performance. Nevertheless, problems may be encountered during expansion of the balloon and deployment of the stent. Frequently the stent does not cover the entire surface of the balloon. Consequently, as the balloon is pressurized, the areas of the balloon not covered by the stent expand first, causing uneven expansion and possibly deformation of the stent. In addition, after the balloon is deflated, it assumes an irregular shape, causing a relatively large effective diameter, and making retraction of the catheter from the vascular system difficult. Because of these limitations, it would be desirable to devise a mechanism for deploying a stent from a catheter that does not require a balloon.

To avoid the need for a balloon, various mechanical means to expand and deploy stents have been disclosed. U.S. Pat. No. 6,217,585 discloses a deployment device that consists of an expansion framework or cage near the distal end of the catheter. The cage consists of elongated strands coupled at opposite ends to the catheter and to a control means at the proximal end of the strands. Axial movement of the control device relative to the catheter either elongates the strands to radially collapse the cage, or axially reduces the distance between the strand ends for radial enlargement. U.S. Pat. No. 6,364,887 discloses a stent deployment device that comprises a catheter with an introducing head near the distal end of the catheter that transports the stent. On the circumference of the introducing head are radially expanding elements such as springs that, when released, press against the inside of the stent and cause it to expand. Both of these inventions have the disadvantage of requiring a fairly complex mechanism to enable the operator to control and engage the expansion mechanism without putting undue force on surrounding tissues.

U.S. Pat. No. 5,902,333 discloses a delivery system that includes a catheter that transports a radially compacted stent or other prosthesis near the distal end of the catheter. The catheter has a dilating tip that is distal to the stent mounting area. Both the proximal and distal portions of the dilating tip are gradually tapered so that the mid-portion of the tip has the largest diameter, and is slightly larger than the diameter of the radially compacted stent. As the catheter is advanced to the treatment site, the distally tapered tip may be used to gently widen the vessel lumen. After the stent is released from the catheter, the dilating tip may be passed through the lumen of the stent as the catheter is retracted, causing the tip to expand the stent to an internal diameter approximately equal to the largest diameter of the tip. Although simple to use, the utility of this device is limited because the diameter of the dilating tip must be smaller than the diameter of the blood vessel, and therefore, smaller than the optimal, final diameter of the deployed stent.

It would be desirable, therefore to provide a device and method delivering and deploying a stent or other prosthesis that would overcome these and other limitations.

SUMMARY OF THE INVENTION

One aspect according to the invention provides a delivery system for a stent that includes a catheter having an elongated inner member and at least one flexible, longitudinally oriented outer member that is operably attached to the distal portion of the inner member. A stent is placed concentrically around the flexible outer member, near the distal end of the catheter. When the elongated inner member is retracted, the flexible outer member folds longitudinally and the stent is deployed to the target site.

Another aspect according to the invention provides a method for delivering a stent to a treatment site within the vascular system. The method includes providing a delivery system that comprises a catheter having an elongated inner member and a flexible, longitudinally oriented outer member that is operably attached to the distal portion of the elongated inner member, and a stent on a distal portion of the flexible outer member of the catheter. The method further includes advancing the delivery device through the vasculature until the distal portion of the device is adjacent to the treatment site, retracting the inner member and thereby causing the flexible outer member to fold longitudinally and the stent to be deployed as a result of the folding of the outer member.

Another aspect of the invention provides a stent delivery device comprising a catheter having an elongated inner member and at least one flexible, longitudinally oriented, outer member that is operably attached to a distal portion of the elongated inner member. Any of a variety of stent designs having a selected diameter may be coupled to the distal portion of the flexible outer sheath of the catheter. When the elongated inner member is retracted, the flexible outer member folds longitudinally adjacent to the lumen of the stent causing the stent to be deployed.

The present invention is illustrated by the accompanying drawings of various embodiments and the detailed description given below. The drawings should not be taken to limit the invention to the specific embodiments, but are for explanation and clarity. The detailed description and drawings are merely illustrative of the invention rather than limiting, the scope of the invention being defined by the appended claims and equivalents thereof. The forgoing aspects and other attendant advantages of the present invention will become more readily appreciated by the detailed description taken in conjunction with the accompanying drawings.

DETAILED DESCRIPTION

Figure 1:
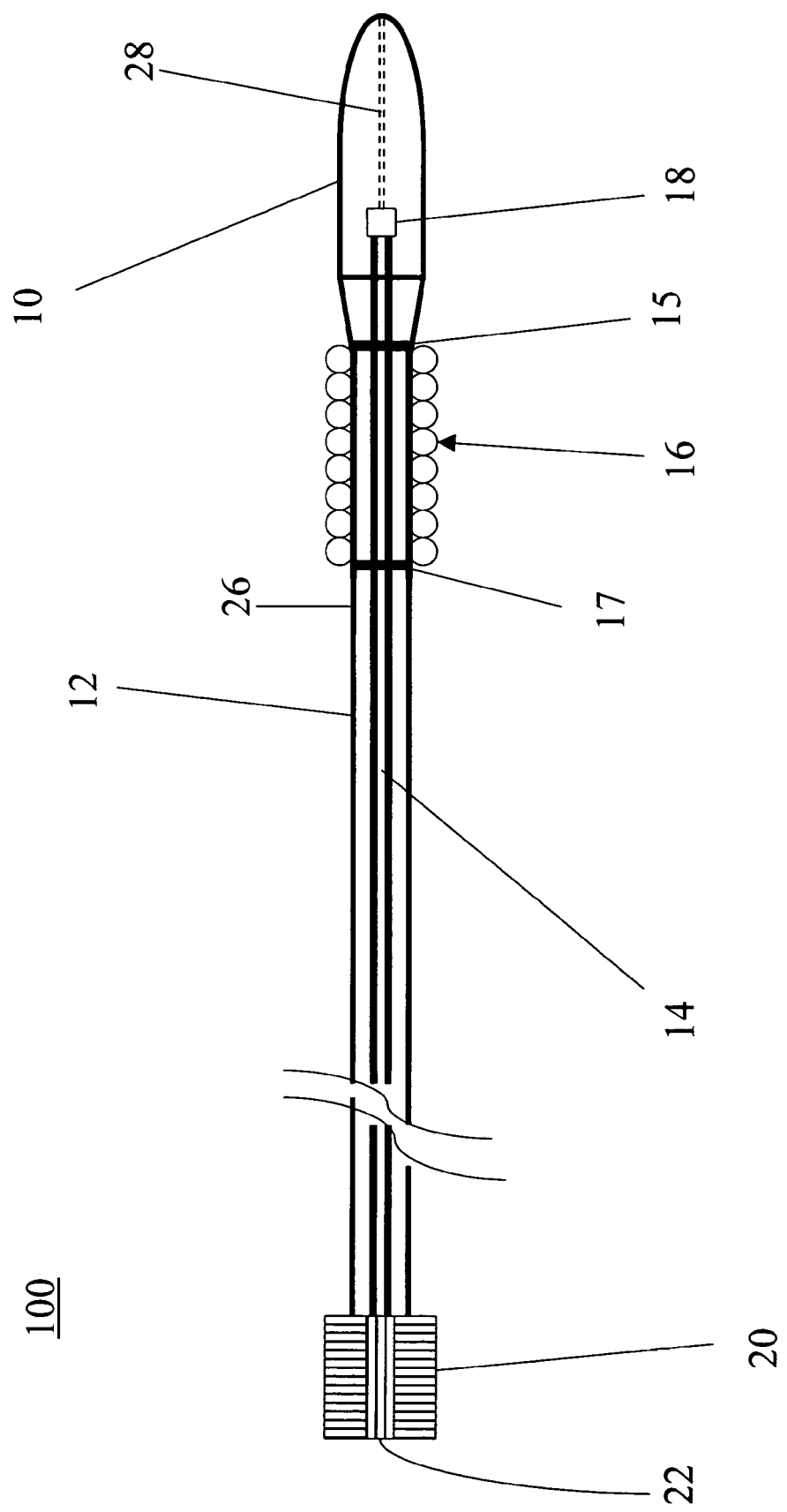
FIG. 1 is a cross sectional side view of a delivery system for stents or other tubular prostheses in which both the inner and outer members are fully extended, in accordance with one aspect of the invention.

Referring to the drawings, FIG. 1 is a side view of a medical device delivery system 100 for treating vascular lesions, according to the present invention. The medical device delivery system comprises a catheter having a distal end cap 10, with an elongated inner member 14 attached to end cap 10. Also attached to distal end cap 10 is flexible outer member 12. In one embodiment, both inner member 14 and outer member 12 are attached to end cap 10 using adhesives. In another embodiment, both inner member 14 and outer member 12 are attached to end cap 10 using fusion bonding. In one embodiment to the invention, a radiopaque marker 18 is embedded in the distal end portion 10 to facilitate placement of the distal tip of the catheter at the desired location in the vascular system.

The distal end portion 10 is comprised of silicone, or a biocompatible polymeric material such as polyurethane, polyethylene or polytetrafluroethylene (PTFE). The use of silicone in certain embodiments may reduce the incidence of vascular tissue damage due to the lubricious surface provided by silicone. The distal portion of end cap 10 is shaped to facilitate passage of the catheter through the vascular system. In various embodiments of the invention, end cap 10 is rounded, tapered or bullet-shaped, among other appropriate shapes. In one embodiment of the invention, the end cap 10 has a lumen 28 that can accommodate a guide wire running longitudinally through the end cap 10. The guide wire is, in one embodiment, of metallic construction, and is inserted into the femoral artery and threaded through the vascular system to the target site. The end cap 10 is then slipped over the guide wire and the catheter is guided along the vascular route, until both the guide wire and catheter are at their desired target locations. The guide wire is then withdrawn from the body. Using fluoroscopy, the radiopaque marker 18 can be observed during the placement procedure, and thereby facilitate placement of the distal tip of the catheter at a desired location.

The inner member 14 comprises a rod or shaft attached at its distal end to end cap 10 and extends the entire length of the catheter. Inner member 14 must be sufficiently flexible so that the catheter can be threaded through the vascular system, but must also have sufficient longitudinal stiffness so that it does not kink during placement of the catheter. Inner member 14 may be made of a metallic material such as stainless steel, titanium or nitinol, or a biocompatible polymeric material such as polyurethane, polyethylene, nylon, PTFE or combinations of these or similar materials. The diameter of inner member 14 is selected to give it the needed longitudinal stiffness and lateral flexibility, and will depend on the properties of the material(s) of which it is composed. Generally, the diameter of inner member 14 will be in the range of 0.2 to 2.0 mm.

Attached to end cap 10 is at least one outer member 12. The primary purpose of outer member 12 is to transport the stent during transit through the vascular system and to deploy the stent at the target site. In one embodiment, outer member 12 is a flexible sheath. Outer member 12 may comprise a flexible, biocompatible, polymeric material such as polyurethane, polyethylene, nylon, or PTFE.

In other embodiments, outer member 12 is a mesh of flexible wires comprising nylon, polyether-block co-polyamide polymers such as Pebax® Resins, a metallic material such as braided stainless steel or polymer-coated, braided stainless steel. The polymer coating comprises nylon, polyether-block co-polyamide polymers such as Pebax® Resins, or any other appropriate polymeric material. A distal portion 26 of outer member 12 holds the stent in place as it is transported through the vascular system. In one embodiment, a stent or other tubular prosthesis 16 is slipped over the distal end of the catheter, positioned over a distal portion 26 of outer member 12 and crimped to a reduced diameter so that the stent 16 is held firmly in place. The diameter of the distal portion 26 of outer member 12 is selected so that the outer diameter of the crimped stent is no greater than the diameter of end cap 10, giving the catheter a smooth outer surface and facilitating its passage through the vascular system. Two radiopaque circumferential bands 15 and 17 are located on inner member 14 at each end of the stent 16, and serve as radiopaque markers so that the precise location of the stent within the vascular system can be observed using fluoroscopy. The radiopaque markers 15, 17, and 18 comprise gold or any other appropriate material. In other embodiments, a plurality of radiopaque circumferential bands 15 are located on the inner member 14.

A hub 20 is attached to the proximal end of outer member 12, and a second hub 22 is attached to the proximal end of inner member 14. In one embodiment, the two hubs are locked to each other as shown in FIG. 1. When the two hubs are locked, the outer member 12 is maintained in a fully extended configuration and held taut between the distal end cap 20 and the locked hubs (20 and 22). This configuration prevents outer member 12 from flexing inward toward the center of the catheter during its passage through the vascular system and releasing the stent prematurely.

Figure 2:
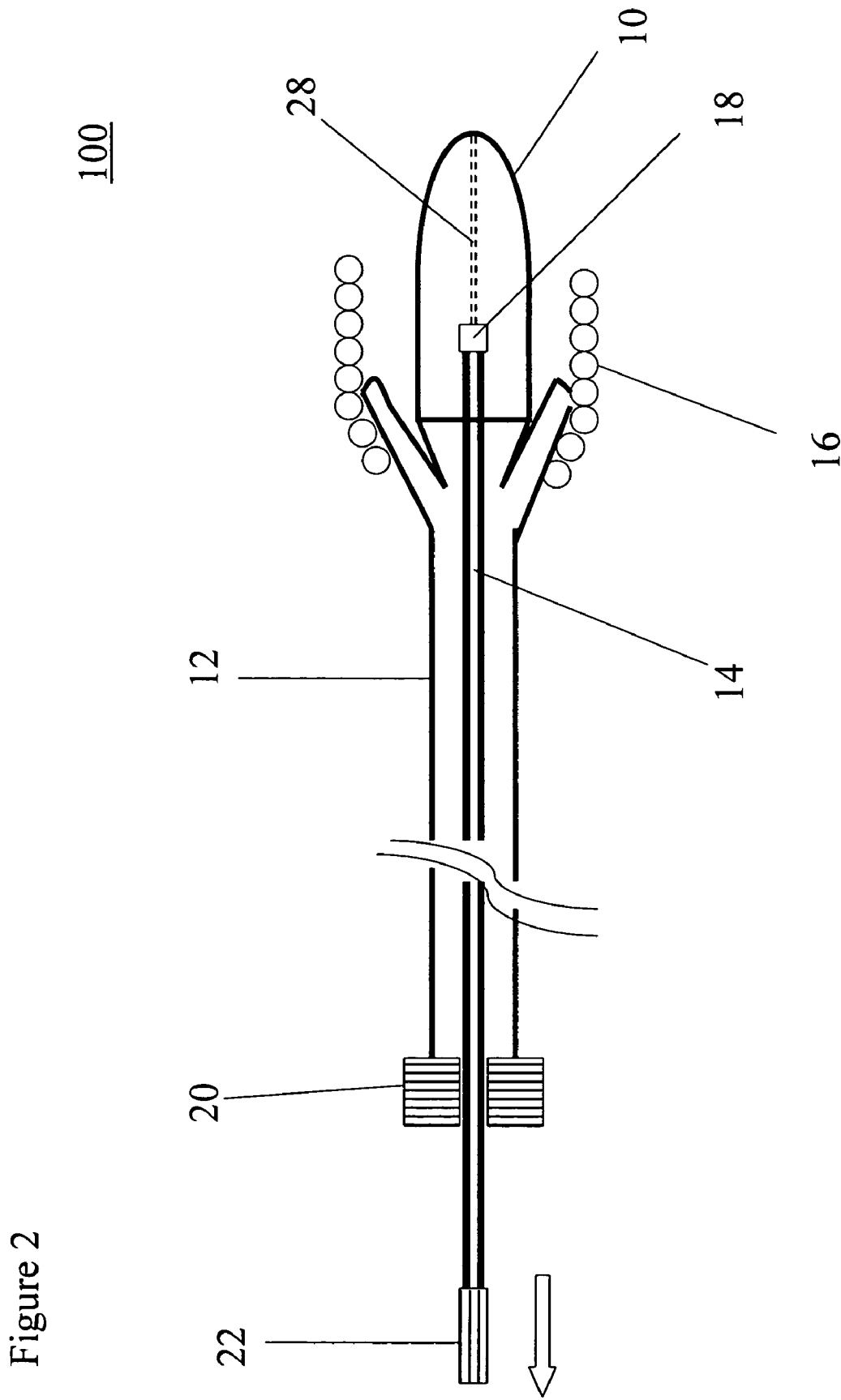
FIG. 2 is a cross sectional side view of a delivery system for stents and other tubular prostheses in which the elongated inner member is partially retracted and the flexible member is partially folded adjacent to the inner side of the stent, in accordance with one aspect of the invention.

When the distal portion of the catheter is placed adjacent to the target site, the hubs 20 and 22 are unlocked from each other, allowing inner member 14 and outer member 12 to move in relation to each other. Inner member 14 is partially retracted as shown in FIG. 2. As inner member 14 is retracted, it draws end cap 10 in a proximal direction, causing the distal portion 26 of outer member 12 to pass over end cap 10, and fold longitudinally (FIG. 2), allowing end cap 10 to move in a proximal direction and pass through the lumen of the stent 16, surrounded by a double layer of outer member 12. The diameter of the combination of end cap 10 and the folded outer member 12 causes the stent 16 to expand and to be deployed from the catheter to the target site. The diameter of end cap 10 and the thickness of the folded outer member 12 are selected so that the combination causes the stent 16 to expand to a predetermined diameter, beginning at the distal end of the stent 16, and progressing to its proximal end. The rate of stent deployment is controlled by the rate at which the operator retracts inner member 14; consequently, the stent may be deployed slowly if so desired. After the stent is deployed, inner member 14 is advanced in a distal direction causing outer member 12 to unfold. When outer member 12 is fully extended, the hubs 20 and 22 will be aligned with each other, and can once again be locked to each other. The catheter will have regained its smooth outer surface and low profile, and may be removed from the patient.

In one embodiment of the invention, the distal portion of outer member 12 is coated with a gel that includes or encapsulates a drug or therapeutic agent. The therapeutic agent or agents may be dispersed within or encased by a polymeric coating, and are eluted at the target site within the vascular system as the stent is deployed. A therapeutic agent is capable of producing a beneficial effect against one or more conditions including coronary restenosis, cardiovascular restenosis, angiographic restenosis, arteriosclerosis, hyperplasia, and other diseases and conditions. The therapeutic agent may comprise, for example an antirestenotic drug, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen a collagenic derivative, a protein, a protein analog, a saccharide, a saccharide derivative, a bioactive agent, a pharmaceutical drug, a therapeutic substance, or combinations thereof.

In one embodiment of the invention, the device can be used to deliver a drug or therapeutic agent into the vascular system. In this embodiment, inner hub 22 includes a port and a means to accommodate a syringe such as a luer fitting, or any other appropriate fitting. Inner member 14 includes a lumen connected to the port at hub 22 and to lumen 28 connecting to an orifice in the distal end cap 10 for delivery of the drug or therapeutic agent. The drug or therapeutic agent may be any of those described above.

Figure 3:
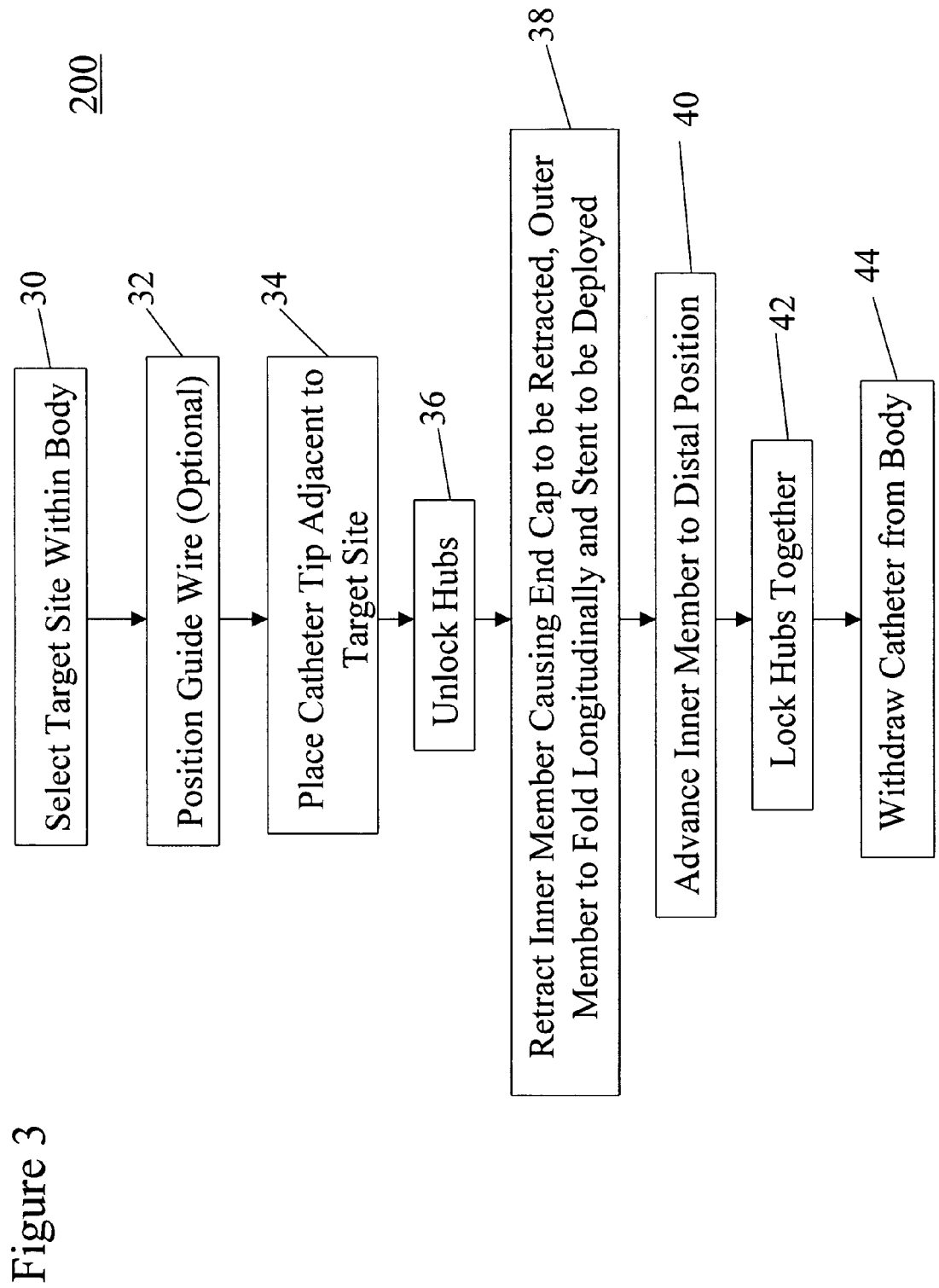
FIG. 3 is a flow diagram of a method of delivering a stent to a treatment site within the vascular system, in accordance with one aspect of the invention.

FIG. 3 is a flowchart illustrating a method 200 for treating a target site within the vascular system by delivering a stent or other tubular prosthesis in accordance with the present invention. The method begins at block 30 wherein a target site is selected. Next, as indicated at block 32, a guide wire may be inserted into the femoral vein or at another site, advanced to the target site, and positioned so that the distal tip of the guide wire is adjacent to the target site. The end cap of the delivery system may be slipped over the guide wire and the catheter threaded through the vascular system. The distal tip of the catheter is placed adjacent to the target site, as indicated in block 34. Next, the hubs at the proximal ends of the inner member and the outer member are unlocked from each other as indicated in block 36. With the hubs unlocked, the inner member and the outer member can be moved in relation to each other.

As indicated in block 38, the inner member is retracted while the outer member remains where it was placed. This causes the end cap to be retracted and drawn into the lumen of the stent, and the distal portion 28 of the outer member to fold longitudinally and pass over the exterior of the end cap 10, as shown in FIG. 2. The diameter of the end cap 10 with the folded outer member surrounding it is larger than the inner diameter of the stent 16, and therefore, causes the stent to expand and be deployed from the catheter. Once the stent is deployed, the inner member may be advanced to its original, distal position, so that the outer member is fully extended, as indicated in block 40. The hubs may then be locked to each other, as in block 42, so that the catheter will have a smooth exterior surface and a constant diameter. Finally, as indicated in block 44, the catheter may be safely removed from the body.

Because the system of the present invention does not require a balloon or other complex apparatus to deploy the stent, it is simple and inexpensive to manufacture compared to previously disclosed stent delivery systems. Further, its low profile makes it comparatively easy to maneuver through the vascular system, and reduces the potential for damage to the vascular tissues. In addition, the delivery system of the present invention can be used with a variety of stent designs and other tubular prostheses, and the rate of delivery may be controlled by the operator.

While the invention has been described with reference to particular embodiments, it will be understood by one skilled in the art that variations and modifications may be made in form and detail without departing from the spirit and scope of the invention.

What is claimed is:

1. A system for treating a vascular condition comprising:
   a catheter including an elongated inner member and at least one flexible longitudinally oriented outer member that is fixedly attached to a distal portion of the elongated inner member, the distal portion of the elongated inner member comprising a cap portion; and
   a stent having a proximal end and a distal end, the stent disposed on a distal portion of the flexible outer member of the catheter, wherein when the elongated inner member is retracted, the flexible outer member folds adjacent an inner side of the stent, causing the stent to be deployed.

2. The system of claim 1 wherein the cap portion has a diameter greater than the diameter of the stent when the stent is disposed on the flexible outer member.

3. The system of claim 1 wherein the cap portion has a bullet shape.

4. The system of claim 1 wherein the stent is deployed by causing it to expand from the distal end to the proximal end.

5. The system of claim 1 further comprising a first hub attached to the proximal end of the elongated inner member and a second hub attached to the proximal end of the outer member of the catheter in a configuration so that the hubs can be locked to each other, whereby, when the hubs are in a locked configuration, the flexible outer member is fully extended, and the outer member and the elongated inner member are maintained in a fixed longitudinal relationship to each other.

6. The system of claim 1 wherein the cap portion comprises silicone.

7. The system of claim 1 wherein the elongated inner member comprises one or more materials selected from the group consisting of metals, titanium, metal alloys, stainless steel, nitinol, polypropylene, polyethylene, medically approved polymers.

8. The system of claim 1 wherein the flexible outer member of the catheter comprises braided stainless steel wire.

9. The system of claim 1 wherein the cap portion includes a radiopaque marker.

10. The system of claim 1 wherein the flexible outer member comprises a plurality of wires.

11. The system of claim 1 wherein the flexible outer member comprises a sheath.

12. The system of claim 1 wherein the distal end of the cap portion is sized to expand the stent to a predetermined diameter.

13. The system of claim 1 wherein the outer member is sized to expand the stent to a predetermined diameter.

14. The system of claim 1 wherein the distal portion of the outer member is coated with a drug-eluting polymer coating.

15. The system of claim 14 wherein the drug-eluting polymer coating comprises a therapeutic agent.

16. The system of claim 15 wherein the therapeutic agent is selected from the group consisting of an antirestenotic drug, an antisense agent, an antineoplastic agent, an antiproliferative agent, an antithrombogenic agent an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen a collagenic derivative, a protein, a protein analog, a saccharide, a saccharide derivative, a bioactive agent, a pharmaceutical drug, a therapeutic substance, or combinations thereof.

17. The system of claim 5 further comprising a fitting configured to accommodate a syringe on the first hub contacting a lumen through the inner member connecting the fitting and a distal portion of the inner member for delivery of a therapeutic agent.

18. A method for treating a vascular condition, the method comprising:
    providing a delivery device including a catheter having an elongated inner member and at least one flexible longitudinally oriented outer member fixedly attached to a distal portion of the elongated inner member, the distal portion of the elongated member comprising a cap portion, and a stent having a proximal end and a distal end, the stent disposed on a distal portion of the flexible outer member of the catheter;
    inserting the delivery device through a vessel proximate the target site;
    retracting the inner member;
    drawing the cap portion into a stent lumen in response to retracting the inner member;
    folding the outer member adjacent an inner side of the stent in response to retracting the inner member; and
    deploying the stent as a result of the folding of the outer member.

19. The method of claim 18 further comprising: adjusting hubs on a proximal portion of the catheter to an unlocked position to allow retraction of the inner member.

20. The method of claim 18 further comprising: advancing the elongated inner member in a distal direction until the flexible outer member is fully extended; and
    adjusting the hubs on the proximal portion of the catheter to a locked position to allow the catheter to be withdrawn from the patient following stent deployment.

* * * * *